United States Patent
Arrieta

(10) Patent No.: US 8,575,430 B2
(45) Date of Patent: Nov. 5, 2013

(54) HYBRID ARTICHOKE VARIETY NUN 4006 AR

(75) Inventor: Ignacio Susín Arrieta, Huesca (ES)

(73) Assignee: Nunhems, B.V., Nunhem (NL)

( * ) Notice: Subject to any disclaimer, the term of this patent is extended or adjusted under 35 U.S.C. 154(b) by 681 days.

(21) Appl. No.: 12/715,664

(22) Filed: Mar. 2, 2010

(65) Prior Publication Data

US 2011/0067142 A1     Mar. 17, 2011

(51) Int. Cl.
| | |
|---|---|
| *A01H 5/10* | (2006.01) |
| *A01H 1/02* | (2006.01) |
| *A01H 4/00* | (2006.01) |
| *C12N 15/82* | (2006.01) |

(52) U.S. Cl.
USPC ........... 800/298; 800/260; 800/265; 800/268; 800/278

(58) Field of Classification Search
None
See application file for complete search history.

(56) References Cited

U.S. PATENT DOCUMENTS

2009/0044299 A1     2/2009    Colfer

FOREIGN PATENT DOCUMENTS

| WO | WO 2006/108697 | 10/2006 |
|---|---|---|
| WO | WO 2007/128559 | 11/2007 |

OTHER PUBLICATIONS

PVP 9000179 (Plant Variety Protection No. 9000179, Jan. 31, 1991).*
Schrader, "Growth Regulator Gives Earlier Harvest in Artichokes," California Agriculture, vol. 48, No. 3, pp. 29-32 (1994).
Ryder et al., Hort. Science, vol. 18, pp. 646-653 (1983).
Meyer and Stasse-Wolthuis, European Journal of Clinical Nutrition, vol. 63, pp. 1277-1289 (2009).
Pecaut et al., Revue Horticuole, vol. 256, pp. 21-26 (1985).

\* cited by examiner

*Primary Examiner* — Shubo (Joe) Zhou
*Assistant Examiner* — Keith Robinson
(74) *Attorney, Agent, or Firm* — Hunton & Williams LLP

(57) ABSTRACT

The invention provides a new and distinct hybrid variety of globe artichoke, NUN 4006 AR or Symphony F1, which is characterized by producing high quality, green heads for the fresh market and/or the processing industry.

25 Claims, No Drawings

HYBRID ARTICHOKE VARIETY NUN 4006 AR

FIELD OF THE INVENTION

The present invention relates to the field of plant breeding. In particular, the invention provides for a new and distinct hybrid variety of Globe artichoke designated NUN 4006 AR (or "Symphony F1"). The new variety produces medium sized heads, suitable for both the fresh market and/or the processing market. The variety is relatively early in time of appearance of the floral heads. The heads have green outer bracts and a triangular shape (in the longitudinal section). The variety is distinct from the most similar hybrid variety, Madrigal F1, by a number of characteristics, such as the earlier time of appearance of the central flower head, the overall plant height being tall, but not as tall as Madrigal F1, with more lateral shoots developing on the main stem than Madrigal F1, and other differences. Provided are seeds of NUN 4006 AR, plants and plant parts produced from these seeds (such as heads, hearts, bottoms, etc.), vegetative reproductions of the variety NUN 4006 AR, and progeny of the variety.

SUMMARY OF THE INVENTION

The invention provides for a new hybrid variety of Globe artichoke called NUN 4006 AR. The invention also provides for a plurality of seeds of the new variety, plants produced from growing the seeds and plant parts obtainable from the grown plant, such as (harvested) flower heads, or parts of the flower heads (e.g. hearts, bottoms, etc).

Thus, in one aspect, the invention provides for seeds of artichoke variety designated NUN 4006 AR, wherein a representative sample of seeds of said variety was deposited under Accession Number PTA 10654.

In another aspect, the invention provides for an artichoke plant of artichoke variety NUN 4006 AR, a representative sample of seed from said variety has been deposited under Accession Number PTA 10654.

In other aspects, the invention provides for plant parts, such as pollen, flower heads, hearts, bottoms, bracts, shoots, cuttings, and receptacles of variety NUN 4006 AR, or parts thereof.

In other aspects, the invention provides for progeny of variety NUN 4006 AR such as progeny obtained by selfing NUN 4006 AR one or more times and/or cross-pollinating NUN 4006 AR with another Globe artichoke plant or variety one or more times. In particular, the invention provides for progeny that retain all the morphological and physiological characteristics of NUN 4006 AR when grown under the same environmental conditions. In another aspect, the invention provides for vegetative reproductions of the variety and essentially derived varieties of NUN 4006 AR.

DEFINITIONS

"Artichoke" or "Globe artichoke" refers herein to plants of the species *Cynara scolymus* L. (synonym *Cynara cardunculus* var. *scolymus* L.)

"Flower head" or "head" refers to immature flower heads (also called "flower buds" or "capitulates"), harvested or on the plant. The "central flower head" refers to the terminal flower head produced on the central, main stem. Other flower heads are produced on lateral branches.

"Heart" is the edible part of the flower head comprising or consisting of the fleshy receptacle (or a part thereof) with the fleshy base of the inner bracts (or parts thereof). "Artichoke bottom" is the edible fleshy lower part of the heart (receptacle).

"UPOV descriptors" are the plant variety descriptors described for Globe Artichoke in the "Guidelines for the Conduct of Tests for Distinctness, Uniformity and Stability," TG/184/3 (Geneva 2001), as published by UPOV (International Union for the Protection of New Varieties and Plants, available on the world wide web at upov.int) and which can be downloaded from the world wide web at upov.int/en/publications/tg_rom/tg_index.html, and is herein incorporated by reference in its entirety.

As used herein, the term "plant" includes the whole plant or any parts or derivatives thereof, preferably having the same genetic makeup as the plant from which it is obtained, such as plant organs (e.g., harvested or non-harvested heads, hearts, receptacles), plant cells, plant protoplasts, plant cell tissue cultures from which whole plants can be regenerated, plant calli, plant cell clumps, plant transplants, seedlings, plant cells that are intact in plants, plant clones or micropropagations, or parts of plants (e.g., harvested tissues or organs), such as plant cuttings, vegetative propagations, embryos, pollen, ovules, fruits, flowers, leaves, seeds, clonally propagated plants, roots, stems, root tips, grafts, parts of any of these and the like. Also any developmental stage is included, such as seedlings, cuttings prior or after rooting, mature plants or leaves.

"Harvested plant material" refers herein to plant parts (e.g., heads detached from the whole plant or hearts removed from the heads) which have been collected for further storage and/or further use.

"Harvested seeds" refers to seeds harvested from a line or variety, e.g., produced after self-fertilization or cross-fertilization and collected.

As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

A variety is referred to as an "Essentially Derived Variety" (EDV) is a variety (i.e., shall be deemed to be essentially derived from another variety, "the initial variety") when (i) it is predominantly derived from the initial variety, or from a variety that is itself predominantly derived from the initial variety, while retaining the expression of the essential characteristics that result from the genotype or combination of genotypes of the initial variety; (ii) it is clearly distinguishable from the initial variety; and (iii) except for the differences which result from the act of derivation, it conforms to the initial variety in the expression of the essential characteristics that result from the genotype or combination of genotypes of the initial variety. Thus, an EDV may be obtained for example by the selection of a natural or induced mutant, or of a somaclonal variant, the selection of a variant individual from plants of the initial variety, backcrossing, or transformation by genetic engineering.

"Plant line" is for example a breeding line which can be used to develop one or more varieties.

"Hybrid variety" or "F1 hybrid" refers to the seeds harvested from crossing two inbred parental lines. For example, the (male-sterile) female parent is pollinated with pollen of the male parent to produce hybrid (F1) seeds on the female parent.

"Average" refers herein to the arithmetic mean.

DETAILED DESCRIPTION

Globe artichoke is a vegetable crop originating from the Mediterranean region. The immature flower heads (also called "globes") contain edible parts, the fleshy bracts and hearts, which can be harvested for the fresh market or for industrial purposes (e.g., the canning industry). Certain extracts are also used in the pharmaceutical field.

Artichoke is predominantly cross-pollinating (due to the stigmatic surfaces maturing several days after pollen shedding) and selfing can result in some inbreeding depression. Artichoke cultivars have traditionally been bred as clones, using vegetative propagation (planting of basal stumps or suckers), because seed populations were not uniform enough for cultivation. In recent years seed propagated hybrid cultivars have been developed which do have good uniformity, such as Madrigal F1, Concerto F1 and others. These hybrids are produced from true breeding inbred parental lines.

The shift to seed-planted varieties (rather than vegetative cultivation) has enabled artichoke to be grown as an annual crop, although seed-planted varieties can also be grown as perennials. Seed plant varieties are cost and labor saving, because seeds are sown mechanically. Also yields and quality are much higher, probably to some extent due to the fact that direct-seeded plants produce long taproots, which penetrate deeper into the soil than the vegetative plantations. Hybrid vigor also plays a role in improved yields, as does the better pest and disease control of annually seeded crops. Although a number of (seed-planted) hybrid varieties exist, there is still a need for new, high yielding, uniform hybrids with good head quality.

A number of characteristics are important to artichoke breeders including (a) the time of harvest (varieties adapted to early or late harvest); (b) the size and quality of the heads (determining whether the heads are suitable for fresh and/or industry purposes); (c) the shape of the heads; (d) the size of the plant; and (e) the spinelessness of the bracts.

The present invention provides a new hybrid variety, NUN 4006 AR, which is relatively early maturing and produces heads suitable for both the fresh market and/or the processing industry. The plants of NUN 4006 AR are most similar to the commercial variety Madrigal F1, which is a processing variety sold by Nunhems B.V. However, NUN 4006 AR differs from Madrigal F1 in a number of characteristics and can easily be distinguished from Madrigal when grown under the same environmental conditions (see Table 2). First, the plants grown from NUN 4006 AR seeds are tall plants (measured from the soil to the top of the central flower head), but on average slightly smaller than the very tall Madrigal plants. The diameter of the main stem of NUN 4006 AR is slightly thinner than that of Madrigal (measured about 10 cm below the central flower head). The leaves of both varieties are similar (long leaves with incisions, slightly erect, without spines), but the leaves of NUN 4006 AR have on average fewer and shorter lobes than those of Madrigal and the lobe tips are nearly at a right-angle, while those of Madrigal are acute. Also the leaf blade color is not as dark green as in Madrigal and the petiole base of NUN 4006 AR has less anthocyanin at the base compared to Madrigal.

Both Madrigal and NUN 4006 AR produce medium sized flower heads on the main stem and on lateral shoots. In the longitudinal section, the shape of the flower heads of NUN 4006 AR is triangular, while that of Madrigal is ovate. In addition, the flower heads of NUN 4006 AR have an acute tip, while those of Madrigal have a rounded tip. As discussed herein, one of the main differences is the time of appearance of the central flower head, which is "late" in Madrigal and "medium" in NUN 4006 AR when grown under the same environmental conditions. If no giberellic acid ($GA_3$) is applied to the plants, then NUN 4006 AR is about 30-40 days earlier than Madrigal F1. $GA_3$ is a plant growth regulator which can be applied one or more times to artichoke plants to initiate and/or advance bolting, bud formation and therefore harvest time (see, e.g., Wayne L. Schrader, California Agriculture 48(3): 29-32, "Growth regulator gives earlier harvest in artichokes."). By, for example, combining production of non-$GA_3$ treated plants with $GA_3$ treated plants, harvest time and harvest period can be optimally controlled.

NUN 4006 AR is typically sown in the USA between February and June, with harvest from about August until about May to June. The variety has a reduced vernalization (chilling) requirement. NUN 4006 AR can be grown as an annual (recommended) and perennial crop.

The outer bracts of the flower heads are green and spineless in both Madrigal and NUN 4006 AR and have a thick base. In Madrigal a mucron is present, which is lacking in the bracts of NUN 4006 AR. Receptacles are similar between the varieties, with a medium thickness. Madrigal has more compact (dense) heads, with a higher number of internal bracts.

Another variety which is similar to NUN 4006 AR is a vegetatively propagated variety called Blanca de Tudela. However, this variety is not a hybrid, has lesser yield and can also be distinguished easily from NUN 4006 AR when grown under the same environmental conditions. The most obvious distinction is that the leaves of Blanca de Tudela are "entire" (not lobed). Other differences are the way of multiplication (clonal versus seed-propagation), the plant height with NUN 4006 AR being taller, the earliness with Blanca de Tudela being earlier. NUN 4006 AR has higher yields and a better performance than Blanca de Tudela, especially under stress conditions (e.g., soil and/or water salinity, cold stress, etc.). NUN 4006 AR also produces better field uniformity (fewer dead plants after planting) and healthier fields.

The morphological and/or physiological differences between NUN 4006 AR and other known varieties can easily be established by growing NUN 4006 AR next to the other varieties (in the same field, under the same environmental conditions), preferably in several locations which are suitable for artichoke cultivation, and measuring morphological and/or physiological characteristics of a number of plants (e.g., to calculate an average value and to determine the variation range/uniformity within the variety).

For example, trials can be carried out in California, USA, whereby e.g., plant height, width, growth habit, side shoot number, foliage density, head size, head shape, head number, head texture, head fragrance, bract size, bract shape, bract texture, bract number, bract color, bract basal thickness, heart shape and size, heart color, papus length and color, head firmness, bract firmness, head gloss, leaf length and width, leaf incisions (serrations), leaf basal angle, leaf length to width ratio, leaf color, leaf texture, leaf venation, leaf basal thickness, distance between incisions, petiole length and width, pest and/or disease resistance/susceptibility can be measured and directly compared. Also post-harvest characteristics of heads can be compared, such as cold storage holding quality (browning), post-harvest oxidation of heads, and juiciness can be measured using known methods (see e.g., US 2009/0044299, paragraph 0016). The morphological and/or physiological characteristics may vary with variation in the environment (such as temperature, light intensity, day length, humidity, soil, fertilizer use), which is why a comparison under the same environmental conditions is preferred.

Colors can best be measured against The Munsell Book of Color (Munsell Color Macbeth Division of Kollmorgan Instruments Corporation).

Seeds of artichoke variety NUN 4006 AR are provided herein, wherein a representative sample of said seeds (2500 seeds) has been deposited, under the Budapest Treaty, with Accession Number PTA 10654.

Seeds of NUN 4006 AR are obtainable by crossing the male parent with the male-sterile female parent and harvesting the seeds produced on the female parent. The resultant NUN 4006 AR seeds can be grown to produce NUN 4006 AR plants. In one embodiment a plurality of NUN 4006 AR seeds are packaged into small and/or large containers (e.g., bags, cartons, cans, etc.). The seeds may be treated with various compounds, such as seed coatings.

Also provided are plants of artichoke variety NUN 4006 AR, or a part thereof, produced from seeds, wherein a representative sample of said seeds has been deposited under Accession Number PTA 10654. Plants of NUN 4006 AR can be produced by seeding directly in the ground (e.g., field) or by germinating the seeds in controlled environment conditions (e.g., greenhouses) and then transplanting the seedlings into the field. (See Smith et al., University of California, Division of Agriculture and Natural Resources publication 7221, "Artichoke production in California," and the world wide web at anrcatalog.ucdavis.edu for cultivation, harvesting, handling and postharvest methods commonly used).

Parts of NUN 4006 AR encompass any cells, tissues, organs obtainable from the seedlings or plants, such as but not limited to: heads, hearts, bottoms, bracts, cuttings, pollen and the like. Such parts can be stored and/or processed further. Encompassed are therefore also food or feed products comprising one or more of such parts, such as canned hearts or bottoms.

In a preferred embodiment, the invention provides for heads of artichoke variety NUN 4006 AR, or a part of the head. The heads are preferably mature heads. They may be harvested (e.g., manually, by removing the heads from the remaining plant) and stored and/or processed further. In another embodiment, the invention provides for a container comprising or consisting of a plurality of heads of NUN 4006 AR.

In yet a further embodiment, the invention provides for a method of producing a new artichoke plant. The method comprises crossing NUN 4006 AR, either as male or as female parent, with a second artichoke plant (or a wild relative of artichoke) one or more times, and/or selfing NUN 4006 AR one or more times, and selecting progeny from said crossing and/or selfing. Progeny are either the generation (seeds) produced from the first cross (F1) or selfing (S1), or any further generation produced by crossing (F2, F3, F4, etc.) and/or selfing (S2, S3, S4, etc.) and/or backcrossing (BC1, BC2, etc.) one or more selected plants of the F1 and/or S1 and/or BC1 generation (or plants of any further generation) with another artichoke plant (and/or with a wild relative of artichoke).

A "wild" relative of artichoke is herein selected from *Cynara cardunculus* var. *sylvestris* (wild cardoon), *Cynara cardunculus* subsp *cardunculus* (cultivated cardoon), *C. baetica, C. algarbiensis, C. syriaca, C. cornigera, C. cyrenaica, C. humilis* and *C. trournefortii*.

The invention provides for methods of producing varieties which retain all the morphological and physiological characteristics of NUN 4006 AR, or EDVs (Essentially Derived Varieties), which may differ from NUN 4006 AR in one, two, three or more morphological and/or physiological characteristics, but which are still genetically closely related to NUN 4006 AR. The relatedness can, for example be determined by fingerprinting techniques (e.g., making use of isozyme markers and/or molecular markers such as SNP markers, AFLP markers, microsatellites, minisatellites, RAPD markers, RFLP markers and others). A plant is "closely related" to NUN 4006 AR if its DNA fingerprint is at least 80%, 90%, 95%, or 98% identical to the fingerprint of NUN 4006 AR.

By crossing and/or selfing also (one or more) single traits may be introduced into NUN 4006 AR (e.g., using backcrossing breeding schemes), while retaining the remaining morphological and physiological characteristics of NUN 4006 AR. For example, disease resistance genes may be introduced, genes responsible for one or more quality traits (such as head quality), yield, etc. Both single genes and QTLs (quantitative trait loci) may be transferred into NUN 4006 AR by breeding with NUN 4006 AR.

Any pest or disease resistance genes may be introduced into NUN 4006 AR, progeny thereof or into an EDV of NUN 4006 AR. Resistance to one or more of the following diseases is preferably introduced into plants of the invention: Powdery mildew, *Verticillium* wilt, *Botrytis* rot, Curly Dwarf Virus and Bacterial Crown rot. Resistance to one or more of the following pests is preferably present or introduced into plants of the invention: artichoke plume moth, aphid resistance, proba bug resistance, two-spotted spider-mite resistance, Chrysanthemum leaf-miner, and Cribate weevil resistance.

Thus, invention also provides a method for developing an artichoke plant in an artichoke breeding program, using an artichoke plant of the invention, or its parts as a source of plant breeding material. Suitable plant breeding techniques are recurrent selection, backcrossing, pedigree breeding, mass selection, mutation breeding, and genetic marker enhanced selection. For example, in one aspect, the method comprises crossing NUN 4006 AR or progeny thereof with a different artichoke plant, and wherein one or more offspring of the crossing are subject to one or more plant breeding techniques selected from the group consisting of recurrent selection, backcrossing, pedigree breeding, mass selection, mutation breeding, and genetic marker enhanced selection.

In one embodiment, NUN 4006 AR may also be mutated and mutated seeds or plants may be selected in order to change one or more characteristics of NUN 4006 AR. Also natural mutants may be identified and used in breeding. Methods such as TILLING and/or EcoTILLING may be applied to artichoke populations in order to identify mutants. Similarly, NUN 4006 AR may be transformed and regenerated, whereby one or more chimeric genes are introduced into the variety. Transformation can be carried out using standard methods, such as *Agrobacterium tumefaciens* mediated transformation, followed by selection of the transformed cells and regeneration into plants. A desired trait can be introduced into NUN 4006 AR, or progeny thereof, by transforming NUN 4006 AR or progeny thereof with a transgene that confers the desired trait, wherein the transformed plant retains all the morphological and physiological characteristics of NUN 4006 AR, or the progeny thereof, and contains the desired trait.

The invention also provides for progeny of artichoke variety NUN 4006 AR obtained by further breeding with NUN 4006 AR. In one aspect, progeny are F1 progeny obtained by crossing NUN 4006 AR with another plant or S1 progeny obtained by selfing NUN 4006 AR. "Further breeding" encompasses traditional breeding (e.g., selfing, crossing, backcrossing), marker assisted breeding, and mutation breeding. In one embodiment, the progeny have all the physiological and morphological characteristics of variety NUN 4006 AR when grown under the same environmental conditions. In another embodiment the progeny are EDVs and/or have one, two, or three distinct traits (qualitative or quantitative) introduced into NUN 4006 AR, while retaining all the other physiological and morphological characteristics of variety NUN 4006 AR when grown under the same environmental conditions.

The variety NUN 4006 AR can also be reproduced using vegetative reproduction methods. Therefore, the invention provides for a method of producing plants, or a part thereof, of variety NUN 4006 AR comprising vegetative propagation of variety NUN 4006 AR. Vegetative propagation comprises regenerating a whole plant from a part of variety NUN 4006 AR, such as a cutting, a cell culture or a tissue culture (e.g., in vitro meristem culture, see Pecaut et al. 1985, Revue Horticuole 256: 21-26), a "stump" (basal stem piece with attached root sections or a rooted section of the crown), suckers derived from NUN 4006 AR, offshoots derived from NUN 4006 AR or ovoli derived from NUN 4006 AR (see Ryder et al., 1983, Hort Science 18: 646-653).

The invention also provides for a vegetatively propagated plant of variety NUN 4006 AR, or a part thereof, having all the morphological and physiological characteristics of NUN 4006 AR when grown under the same environmental conditions.

Also provided are plant parts derived from variety NUN 4006 AR, or from a vegetatively propagated plant of NUN 4006 AR, being selected from the group consisting of: harvested flower heads or parts thereof, pollen, cells, leaves or parts thereof, petioles, shoots or parts thereof, stems or parts thereof, roots or parts thereof, cuttings, stumps, suckers, offshoots, ovoli, receptacles or parts thereof, bracts or parts thereof, flowers, florets, or flower buds.

Globe artichoke leaves represent a natural source of phenolic acids with dicaffeoylquinic acids, such as cynarin (1,3-dicaffeoylquinic acid), along with its biosynthetic precursor chlorogenic acid (5-caffeoylquinic acid) as the most abundant molecules. In various pharmacological test systems, artichoke leaf extracts have exhibited hepatoprotective, anticarcinogenic, antioxidative, antibacterial, anti-HIV, bile-expelling, and urinative activities as well as the ability to inhibit cholesterol biosynthesis and LDL oxidation. These broad therapeutic indications probably cannot be ascribed to a single, but to several active compounds that together generate additive or synergistic pharmacologic effects; these include mono- and dicaffeoylquinic acids, and flavonoids such as luteolin and its 7-O-glucoside. Artichoke tissues such as leaves, external bracts and stems can be used as a source of inulin and/or phenolics, useful for the production of food additives and nutraceuticals.

In one embodiment, the invention provides for extracts of a plant described herein and compositions comprising or consisting of such extracts. In a preferred embodiment, the extract consists of or comprises tissue of a plant described herein or is obtained from such tissue. For example cynarin may be an extract obtained from leaf tissue and used to make a health-beneficial composition (e.g., a pharmaceutical composition or a food supplement). Likewise inulin (e.g., very long chain inulin, VLCI) may be extracted from globe artichoke tissue, such as roots and used in food or feed, food supplement, pharmaceutical or nutraceutical compositions. VCLI from Globe artichoke has health beneficial properties, e.g., on gut-health, see e.g. WO 2006/108697, WO2007/128559 and Meyer and Stasse-Wolthuis, 2009 (European Journal of Clinical Nutrition 63, 1277-1289).

The invention also provides for a food or feed product comprising or consisting of a plant part described herein and/or an extract from a plant part described herein. The food or feed product may be fresh or processed, e.g., canned, steamed, boiled, fried, etc.

For example, containers such as cans, boxes, crates, bags, cartons, Modified Atmosphere Packagings, films (e.g. biodegradable films), etc. comprising plant parts of plants (fresh and/or processed) described herein are also provided herein.

Marketable heads are generally sorted by size and quality after harvest. Cartons may be packaged with "18s" (18 heads, each larger than 4.5 inches in diameter), "24s" (25 heads of 4-4.5 inches), "36s" (36 heads of 3.5-4 inches), "48$^{ths}$" (48 heads of 3-3.5 inches) or "60s" (60 heads of 2.75-3 inches).

All documents (e.g., patent publications) are herein incorporated by reference in their entirety.

EXAMPLES

Development of NUN 4006 AR

The hybrid NUN 4006 AR was developed from a clone of INTRA (France) and a proprietary line of Nunhems obtained in Picanya, Spain. Inbred parental lines were developed from these lines through several generations of self-pollination and continued selection. The maternal inbred parent of NUN 4006 AR is a vegetative propagated proprietary line of Nunhems, which is male-sterile. The male inbred parent of NUN 4006 AR is a proprietary line of Nunhems propagated by seeds. The female and male parents were crossed to produce hybrid (F1) seeds of NUN 4006 AR. The seeds of NUN 4006 AR can be grown to produce hybrid plants and parts thereof (e.g. flower heads). The hybrid NUN 4006 AR can be propagated by seeds or vegetative.

A total of 2500 seeds of the hybrid variety NUN 4006 AR (also called "Symphony" or "Symphony F1") were deposited on Feb. 17, 2010, at the American Type Culture Collection (ATCC), 10801 University Boulevard, Manassas, Va. 20110-2209 USA. The deposit has been assigned Accession Number PTA 10654. Access to this deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application, or under the Plant Variety Protection Act (7 USC 2321 et seq.).

Characteristics of NUN 4006 AR

Table 1 shows morphological and physiological distinguishing characteristics of NUN 4006 AR compared to two similar varieties, Blanca de Tudela (a vegetatively propagated green variety) and Madrigal F1 (a seed propagated green hybrid variety sold by Nunhems B.V. for industrial use).

TABLE 1

| Morphological and Physiological Characteristic | Blanca de Tudela | Madrigal F1 | NUN 4006 AR (Symphony F1) |
|---|---|---|---|
| Leaf Incision | Incisions absent ("entire") | Incisions present (lobed); many lobes | Incisions present (lobed); medium number of lobes |
| Central flower head - time of appearance | Very early | Late | Medium |

TABLE 1-continued

| Morphological and Physiological Characteristic | Blanca de Tudela | Madrigal F1 | NUN 4006 AR (Symphony F1) |
|---|---|---|---|
| Plant height (With central flower head) | Medium-small | Very tall | Tall |

Table 2 shows the UPOV descriptors of Madrigal F1 (non-patented) and NUN 4006 AR (Symphony F1). The values in bold highlight the characteristics, which can be used to distinguish Madrigal F1 from NUN 4006 AR, when grown under the same environmental conditions.

TABLE 2

| UPOV Number | UPOV descriptor | Madrigal F1 | NUN 4006 AR |
|---|---|---|---|
| 1 | Plant: height (including central flower head) 3 = short, 5 = medium, 7 = tall | 8 | 7 |
| 2 | Plant: Number of lateral shoots on main stem 3 = few, 5 = medium, 7 = many | 3 | 6 |
| 3 | Main stem: height (excluding central flower head) 3 = short, 5 = medium, 7 = tall | 8 | 6 |
| 4 | Main stem: distance between central flower head and youngest well developed leaf | 5 | 5 |
| 5 | Main stem: diameter (at about 10 cm below central flower head) 3 = small, 5 = medium, 7 = large | 7 | 4 |
| 6 | Leaf: attitude (10-12 leaf stage) 1 = erect, 3 = semi-erect, 5 = horizontal | 4 | 3 |
| 7 | Leaf: long spines 1 = absent, 9 = present | 1 | 1 |
| 8 | Leaf: length 3 = short, 5 = medium, 7 = long | 8 | 7 |
| 9 | Leaf: incisions (10-12 leaf stage) 1 = absent, 9 = present | 9 | 9 |
| 10 | Leaf: number of lobes 3 = few, 5 = medium, 7 = many | 7 | 5 |
| 11 | Leaf: length of the longest lobe 3 = short, 5 = medium, 7 = long | 7 | 5 |
| 12 | Leaf: width of the longest lobe 3 = narrow, 5 = medium, 7 = broad | 6 | 6 |
| 13 | Lobe: shape of tip (excluding terminal lobe) 1 = acute, 2 = nearly right angle, 3 = obtuse | 1 | 2 |
| 14 | Lobe: Number of secondary lobes 1 = non or very few, 3 = few, 5 = medium, 7 = many, 9 = very many | 6 | 5 |
| 15 | Lobe: shape of tip of secondary lobes 1 = acuminate, 2 = acute, 3 = rounded | 3 | 3 |
| 16 | Leaf blade: shape in cross section 1 = flat, 2 = V-shaped | 2 | 2 |
| 17 | Leaf blade: intensity of green color (upper side) 3 = light, 5 = medium, 7 = dark | 7 | 5 |
| 18 | Leaf blade: hue of green color 1 = absent, 2 = yellowish, 3 = greenish | 1 | 1 |
| 19 | Leaf blade: intensity of grey hue 3 = weak, 5 = medium, 7 = strong | 3 | 3 |
| 20 | Leaf: hairiness on upper side 1 = absent or very weak, 3 = weak, 5 = medium, 7 = strong, 9 = very strong | 3 | 3 |
| 21 | Leaf blade: blistering 1 = absent or very weak, 3 = weak, 5 = medium, 7 = strong, 9 = very strong | 1 | 1 |
| 22 | Petiole: anthocyanin coloration at base 1 = absent or very weak, 3 = weak, 5 = medium, 7 = strong, 9 = very strong | 5 | 2 |
| 23 | Central flower head: length 3 = short, 5 = medium, 7 = long | 6 | 6 |
| 24 | Central flower head: diameter 3 = small, 5 = medium, 7 = large | 5 | 4 |
| 25 | Central flower head: size 3 = small, 5 = medium, 7 = large | 5 | 5 |
| 26 | Central flower head: shape in longitudinal section 1 = circular, 2 = broad elliptic, 3 = ovate, 4 = triangular, 5 = transverse broad elliptic | 3 | 4 |
| 27 | Central Flower head: shape of tip 1 = acute, 2 = rounded, 3 = flat, 4 = depressed | 2 | 1 |
| 28 | Central flower head: time of appearance 3 = early, 5 = medium, 7 = late | 7 | 5 |
| 29 | Central flower head: time of beginning of opening 3 = early, 5 = medium, 7 = late | 6 | 5 |
| 30 | First flower head on lateral shoot: length 3 = short, 5 = medium, 7 = long | 6 | 6 |
| 31 | First flower head on lateral shoot: diameter 3 = small, 5 = medium, 7 = large | 4 | 4 |
| 32 | First flower head on lateral shoot: size 3 = small, 5 = medium, 7 = large | 4 | 4 |
| 33 | First flower head on lateral shoot: shape in longitudinal section 1 = circular, 2 = broad elliptic, 3 = ovate, 4 = triangular, 5 = transverse broad elliptic | 3 | 4 |
| 34 | First flower head on lateral shoot: Degree of opening 3 = weak, 5 = medium, 7 = strong | 2 | 2 |
| 35 | Outer bract: length of base 3 = short, 5 = medium, 7 = long | 4 | 5 |
| 36 | Outer bract: width of base 3 = narrow, 5 = medium, 7 = broad | 6 | 5 |
| 37 | Outer bract: thickness at base 3 = thin, 5 = medium, 7 = thick | 7 | 7 |
| 38 | Outer bract: main shape 1 = broader than long, 2 = as broad as long, 3 = longer than broad | 3 | 3 |
| 39 | Outer bract: shape of apex 1 = acute, 2 = flat, 3 = emarginated | 2 | 3 |
| 40 | Outer bract: depth of emargination 3 = shallow, 5 = medium, 7 = deep | 4 | 4 |
| 41 | Outer bract: Color (external side) 1 = green, 2 = green striped with violet, 3 = violet striped with green, 4 = mainly violet, 5 = entirely violet | 1 | 1 |
| 42 | Outer bract: hue of secondary color (as 41) 1 = absent, 2 = bronze, 3 = grey | 1 | 1 |
| 43 | Outer bract: reflexing of tip 1 = absent, 9 = present | 1 | 1 |
| 44 | Outer bract: size of spine 1 = absent or very small, 3 = small, 5 = medium, 7 = large, 9 = very large | 1 | 1 |
| 45 | Outer bract: mucron 1 = absent, 9 = present | 9 | 1 |
| 46 | Central flower head: anthocyanin coloration of inner bracts 1 = absent or very weak, 3 = weak, 5 = medium, 7 = strong, 9 = very strong | 1 | 3 |

TABLE 2-continued

| UPOV Number | UPOV descriptor | Madrigal F1 | NUN 4006 AR |
|---|---|---|---|
| 47 | Central flower head: density of inner bracts<br>3 = sparse, 5 = medium, 7 = dense | 7 | 6 |
| 48 | Receptacle: diameter<br>3 = small, 5 = medium, 7 = large | 4 | 3 |
| 49 | Receptacle thickness<br>3 = thin, 5 = medium, 7 = thick | 5 | 5 |
| 50 | Receptacle: shape in longitudinal section<br>1 = flat, 2 = slightly depressed, 3 = strongly depressed | 2 | 2 |
| 51 | Tendency to produce lateral shoots on base<br>3 = weak, 5 = medium, 7 = strong | 6 | 5 |

The invention claimed is:

1. A seed of artichoke variety NUN 4006 AR, wherein a representative sample of said seed has been deposited under Accession Number PTA 10654.

2. A plant of artichoke variety NUN 4006 AR, or a part thereof, wherein a representative sample of seed of said variety has been deposited under Accession Number PTA 10654.

3. A head of artichoke variety NUN 4006 AR, or a part thereof, produced from the plant of claim 2.

4. A method of producing an artichoke plant, comprising crossing the plant of claim 2 with a second artichoke plant one or more times, and selecting progeny from said crossing.

5. A method of producing an artichoke plant, comprising selfing the plant of claim 2 one or more times, and selecting progeny from said selfing.

6. Progeny of the plant of claim 2, wherein said progeny have all the physiological and morphological characteristics of variety NUN 4006 AR when grown under the same environmental conditions.

7. An Essentially Derived Variety of NUN 4006 AR having one, two or three physiological and/or morphological characteristics which are different from those of NUN 4006 AR and which otherwise has all the physiological and morphological characteristics of NUN 4006 AR, wherein a representative sample of seed of variety NUN 4006 AR has been deposited under Accession Number PTA 10654.

8. A method of producing plants, or a part thereof, of variety NUN 4006 AR comprising vegetative propagation of variety NUN 4006 AR, wherein a representative sample of seed variety NUN 4006 AR has been deposited under Accession Number PTA 10654.

9. The method of claim 8, wherein said vegetative propagation comprises regenerating a whole plant from a part of variety NUN 4006 AR.

10. The method of claim 9, wherein said part is a cutting, a cell culture or a tissue culture.

11. A vegetative propagated plant of variety NUN 4006 AR, or a part thereof, having all the morphological and physiological characteristics of NUN 4006 AR when grown under the same environmental conditions, wherein a representative sample of seed of variety NUN 4006 AR has been deposited under Accession Number PTA 10654.

12. Plant parts of variety NUN 4006 AR, or of a plant of claim 11 wherein said plant parts are harvested flower heads or parts thereof, pollen, cells, leaves or parts thereof, petioles, shoots or parts thereof, stems or parts thereof, roots or parts thereof, cuttings, stumps, offshoots, ovoli, receptacles or parts thereof, bracts or parts thereof, flowers, florets, or flower buds, wherein a representative sample of seed of variety NUN 4006 AR has been deposited under Accession Number PTA 10654.

13. A tissue of the plant of claim 2.

14. A tissue of a plant part of claim 12.

15. A food or feed product comprising a plant part of claim 12.

16. The food or feed product of claim 15, wherein said plant part is fresh or processed.

17. A method of producing an artichoke plant having a desired trait, wherein the method comprises transforming the artichoke plant of claim 2 with a transgene that confers the desired trait, wherein the transformed plant retains all the phenotypic and morphological characteristics of variety NUN 4006 AR and contains the desired trait, a representative sample of seed of said variety NUN 4006 AR having been deposited under Accession Number PTA 10654.

18. An artichoke plant produced by the method claim 17, wherein the plant comprises the desired trait and all of the physiological and morphological characteristics of NUN 4006 AR.

19. A method of introducing a single locus conversion into NUN 4006 AR comprising
(a) crossing a plant of variety NUN 4006 AR, a representative sample of seed of said variety having been deposited under Accession Number PTA 10654, with a second plant comprising a desired single locus to produce F1 progeny plants;
(b) selecting F1 progeny plants that have the single locus to produce selected F1 progeny plants;
(c) crossing the selected progeny plants with at least a first plant of NUN 4006 AR to produce backcross progeny plants;
(d) selecting backcross progeny plants that have the single locus and physiological and morphological characteristics of NUN 4006 AR to produce selected backcross progeny plants; and
(e) repeating steps (c) and (d) one or more times in succession to produce selected second or higher backcross progeny plants that comprise the single locus and otherwise comprise all of the physiological and morphological characteristics of NUN 4006 AR when grown in the same environmental conditions.

20. The method of claim 19, wherein the single locus confers a trait, wherein the trait is pest resistance or disease resistance.

21. The method of claim 20, wherein the trait is disease resistance and the resistance is conferred to powdery mildew, Verticillium wilt, Botrytis rot, Curly Dwarf Virus, or Bacterial Crown rot.

22. The method of claim 20, wherein the trait is pest resistance and the resistance is conferred to artichoke plume moth, aphid resistance, proba bug resistance, two-spotted spidermite resistance, Chrysanthemum leaf-miner, or Cribate weevil.

23. A cell or tissue culture produced from a plant of claim 2.

24. An artichoke plant regenerated from a cell or tissue culture of claim 23, said plant expressing all the morphological and physiological characteristics of NU 4006 AR, wherein a representative sample having been deposited under Accession Number PTA 10654.

25. The Essentially Derived Variety of claim 7, wherein said Essentially Derived Variety is obtained by
the selection of a natural or induced mutant, or of a somaclonal variant;
the selection of a variant individual from plants of the initial variety; or
backcrossing, or transformation by genetic engineering.

* * * * *